United States Patent
Buschmann

(10) Patent No.: US 9,351,820 B2
(45) Date of Patent: May 31, 2016

(54) DEVICE FOR REPAIR SURGERY OF CYLINDRICAL ORGANS, PARTICULARLY RUPTURED TENDONS

(75) Inventor: Johanna Buschmann, Zürich (CH)

(73) Assignee: University of Zurich (CH)

(*) Notice: Subject to any disclaimer, the term of this patent is extended or adjusted under 35 U.S.C. 154(b) by 0 days.

(21) Appl. No.: 14/240,115

(22) PCT Filed: Aug. 26, 2012

(86) PCT No.: PCT/EP2012/066564
§ 371 (c)(1),
(2), (4) Date: Apr. 21, 2014

(87) PCT Pub. No.: WO2013/026937
PCT Pub. Date: Feb. 28, 2013

(65) Prior Publication Data
US 2014/0324078 A1  Oct. 30, 2014

(30) Foreign Application Priority Data

Aug. 25, 2011  (EP) .................................. 11178917

(51) Int. Cl.
*A61F 2/00* (2006.01)
*A61B 17/30* (2006.01)
(Continued)

(52) U.S. Cl.
CPC ........... *A61F 2/0063* (2013.01); *A61B 17/1146* (2013.01); *A61B 17/30* (2013.01);
(Continued)

(58) Field of Classification Search
CPC ............... A61B 17/11; A61B 17/1146; A61B 2017/1125; A61F 2/0063
See application file for complete search history.

(56) References Cited

U.S. PATENT DOCUMENTS 4,400,833 A * 8/1983 Kurland ............. A61B 17/1146
                                                         623/1.32
6,656,216 B1 * 12/2003 Hossainy ................. A61F 2/91
                                                         623/1.13
(Continued)

FOREIGN PATENT DOCUMENTS

WO  WO 2008/154035 A1  12/2008
WO  WO 2011003422 A1 *  1/2011

OTHER PUBLICATIONS

Henry, J.A. Burugapalli, K., Neuenschwander, P., and Pandit, A., 2009, Structural variants of biodegradable polyesterurethane in vivo evoke a cellular and angiogenic response that is dictated by architecture, Acta Biomaterialia, p. 29-42.*

(Continued)

*Primary Examiner* — Thomas J Sweet
*Assistant Examiner* — Daniel Bissing
(74) *Attorney, Agent, or Firm* — George Pappas

(57) ABSTRACT

A device for repair surgery of cylindrical organs, particularly ruptured tendons, is configured as a tubular sheath (T) made of a biocompatible and biodegradable polymer. The tubular sheath comprises an elastic fiber mesh formed by electrospinning of said polymer and has an inner wall surface and an outer wall surface substantially parallel thereto. One of said wall surfaces is comparatively rough ($W_R$) and the other one of said wall surfaces is comparatively smooth ($W_S$), with the tubular sheath having a Young elasticity modulus of about 2 to about 5 MPa and an elongation at break of about 50 to about 1,000%. Preferably, the polymer is a biodegradable polyester urethane block copolymer with poly-hydroxy-butyrate as a hard 10 segment and ε-caprolactone as a soft segment.

19 Claims, 2 Drawing Sheets

(51) Int. Cl.

| | |
|---|---|
| *A61B 17/11* | (2006.01) |
| *A61L 27/18* | (2006.01) |
| *A61L 27/50* | (2006.01) |
| *A61L 27/56* | (2006.01) |
| *A61L 27/58* | (2006.01) |
| *A61F 2/08* | (2006.01) |
| *A61L 31/16* | (2006.01) |

(52) U.S. Cl.
CPC .............. *A61F 2/0811* (2013.01); *A61L 27/18* (2013.01); *A61L 27/50* (2013.01); *A61L 27/56* (2013.01); *A61L 27/58* (2013.01); *A61L 31/16* (2013.01); *A61F 2002/0072* (2013.01); *A61L 2430/10* (2013.01)

(56) References Cited

U.S. PATENT DOCUMENTS

| | | | | |
|---|---|---|---|---|
| 2006/0178477 | A1* | 8/2006 | Neuenschwander | A61L 17/10 525/85 |
| 2007/0250112 | A1* | 10/2007 | Ravikumar | A61B 17/221 606/205 |
| 2007/0299542 | A1* | 12/2007 | Mathisen et al. | 623/23.75 |
| 2009/0306775 | A1 | 12/2009 | Macossay-Torres | |
| 2011/0039101 | A1 | 2/2011 | Chang et al. | |
| 2011/0224702 | A1* | 9/2011 | Van Kampen | A61F 2/08 606/151 |
| 2011/0282448 | A1* | 11/2011 | Paulos | A61B 19/026 623/13.11 |
| 2011/0288565 | A1* | 11/2011 | Kubiak | A61B 17/1146 606/151 |
| 2013/0013065 | A1* | 1/2013 | Bills | A61B 17/1146 623/13.15 |

OTHER PUBLICATIONS

Henry, J.A. Burugapalli, K., Neuenschwander, P., and Pandit, A., 2009, Structural variants of biodegradable polyesterurethane in vivo envoke a cellular and angiogenic response that is dictated by architecture, Acta Biomaterialia, p. 29-42.*

Abdelhamid, M.M., Histopathy of the tensor tympani Muscle in Otitis Media, 1989.*

Henry, J.A., Burugapalli, K., Neuenschwander, P., and Pandit, A., 2009, Structural variants of biodegradable polyesterurethane in vivo evoke a cellular and angiogenic response that is dictated by architecture, Acta Biomaterialia, p. 29-42.

Henry, J.A., Simonet, M., Pandit, A., Neuenschwander, P., 2007, Characterization of a slowly degrading biodegradable polyesterurethane for tissue engineering scaffolds, Journal of Biomedical Materials Research Part A, p. 669-679.

Milleret, V., Simone, B., Neuenschwander, P., and Hall, H., 2011, Tuning electrospinning parameters for production of 3D-Fiber-Fleeces with increased porosity for soft tissue engineering applications, European Cells and Materials, vol. 21, p. 286-303.

Bullough, R., Finnigan, T., Kay, A., Maffulli, N., and Forsyth, N., 2008, Tendon repair through stem cell intervention: Cellular and molecular approaches, Disability and Rehabilitation, p. 1746-1751.

Buschmann, J., Müller, A., Feldman, K., Tervoort, T., Fessel, G., Snedeker, J., Giovanoli, P., and Calcagni, M., 2011, Small hook thread (Quill) and soft felt internal splint to increase the primary repair strength of lacerated rabbit Achilles tendons: Biomechanical analysis and considerations for hand surgery, Clinical Biomechanics, p. 626-631.

Chong, A., Ang, A., Goh, J., Hui, J., Lim, A., Lee, E., and Lim, B., 2007, Bone Marrow-Derived Mesenchymal Stem Cells Influence Early Tendon-Healing in a Rabbit Achilles Tendon Model, The Journal of Bone & Joint Surgery, p. 74-81.

Corsi, K., Schwarz, E., Mooney, D., Huard, J., 2007, Regenerative Medicine in Orthopaedic Surgery, Journal of Orthopaedic Research, p. 1261-1268.

Costa, M., Wu, C., Pham, B., Chong, A., Pham, H., and Chang, J., 2006, Tissue Engineering of Flexor Tendons: Optimization of Tenocyte Proliferation Using Growth Factor Supplementation, Tissue Engineering, vol. 12, No. 7, p. 1937-1943.

de Wit, T., de Putter, D., Tra, W., Rakhorst, H., van Osch, G., Hovius, S., van Neck, J., 2009, Auto-Crosslinked Hyaluronic Acid Gel Accelerates Healing of Rabbit Flexor Tendons in Vivo, Journal of Orthopaedic Research, p. 408-415.

Dürselen, L., Dauner, M., Hierlemann, H., Planck, H., Claes, L., and Ignatius, A., 2001, Resorbable Polymer Fibers for Ligament Augmentation, Journal of Biomedical Materials Research, p. 666-672.

Ehrbar, M., Rizzi, S., Hlushchuk, R., et al, 2007, Enzymatic formation of modular cell-instructive fibrin analogs for tissue engineering, Biomaterials, p. 3856-3866.

Ehrbar, M., Schoenmakers, R., Christen, E., Fussenegger, M., and Weber, W., 2008, Drug-sensing hydrogels for the inducible release of biopharmaceuticals, Nature Materials, p. 800-804.

Hänseler, P., Ehrbar, M., Jung, U., Jung, R., Hämmerle, C., and Weber, F., 2010, Bone Morphogenetic Protein-2—Adsorption and Release Behaviour on Clinically Relevant Materials, Bone 46, Section 108, p. S49.

Jo, Y., Rizzi, S., Ehrbar, M., Weber, F., Hubbell, J., and Lutolf, M., 2010, Biomimetic PEG hydrogels crosslinked with minimal plasmin-sensitive tri-amino acid peptides, Journal of Biomedical Materials Research Part A, p. 870-877.

Khanna, A., Friel, M., Gougoulias, N., Longo, U., and Maffulli, N., 2009, Prevention of adhesions in surgery of the flexor tendons of the hand: what is the evidence?, British Medical Bulletin, 90: 85-109.

Komatsu, F., Mod, R., Uchio, Y., and Hatanaka, H., 2007, Optimum location of knot for tendon surgery in side-locking loop technique, Clinical Biomechanics, p. 112-119.

Kuwata S., Yotsumoto, T., and Uchio, Y., 2007, Flexor tendon repair using the two-strand side-locking loop technique to tolerate aggressive active mobilization immediately after surgery, Clinical Biomechanics, p. 1083-1087.

Lendlein, A., Neuenschwander, P., and Suter, U., 1998, Tissue-compatible multiblock copolymers for medical applications, controllable in degradation rate and mechanical properties, Macromolecular Chemistry and Physics, p. 2785-2796.

Lendlein, A., Neuenschwander, P., and Suter, U., 2000, Hydroxytelechelic copolyesters with well defined sequence structure through ring-opening polymerization, Macromolecular Chemistry and Physics, p. 1067-1076.

Maurus, C.F., Schneider, M.K.J., Schmidt, D., Zund, G., and Seebach, J.D., 2006, Activation of human microvascular endothelial cells with TNF-alpha and hypoxia/reoxygenation enhances NK-cell adhesion, but not NK-cytotoxicity, Transplantation, p. 1204-1211.

Milleret, V., Simonet, M., Bittermann, A.G., Neuenschwander, P., and Hall, H., 2009, Cyto-and Hemocompatibility of a Biodegradable 3D-Scaffold Material Designed for Medical Applications, Journal of Biomedical Materials Research Part B—Applied Biomaterials, p. 109-121.

Rodeo, S.A., Potter, H.G., Kawamura, S., Turner, A.S., Kim, H.J., and Atkinson, B.L., 2007, Biologic augmentation of rotator cuff tendon-healing with use of a mixture of osteoinductive growth factors, Journal of Bone and Joint Surgery—American Volume, p. 2485-2497.

Russel, W.M.S., and Burch, R.L., 1959, The principle of humane experimental technique, London, Universities Federation for Animal Welfare, Chapter 4.

Saad B., Kuboki Y., Welti M., Uhlschmid G.K., Neuenschwander P., and Suter U.W., 1999, DegraPol-Foam: A degradable and highly porous polyesterurethane foam as a new substrate for bone formation, 12th World Congress of the European-Society-for-Artificial-Organs, Blackwell Science Inc., p. 939-945.

Sahoo S., Toh S.L., and Goh J.C.H., 2010, PLGA nanofiber-coated silk microfibrous scaffold for connective tissue engineering, Journal of Biomedical Materials Research Part B-Applied Biomaterials, p. 19-28.

Seeherman H.J., Archambault J.M., Rodeo S.A., Turner A.S., D'Augusta D., Li X.J., et al., 2008, rhBMP-12 Accelerates Healing of Rotator Cuff Repairs in a Sheep Model, Journal of Bone and Joint Surgery-American Volume, p. 2206-2219.

(56) References Cited

OTHER PUBLICATIONS

Sharma P., and Maffulli N., 2006, Biology of tendon injury: healing, modeling and remodeling, Journal of Musculoskeletal Neuronal Interaction, p. 181-190.

Simonet M., Schneider O.D., Neuenschwander P., and Stark W.J., 2007, Ultraporous 3D polymer meshes by low-temperature electrospinning: Use of ice crystals as a removable void template, Polymer Engineering and Science, p. 2020-2026.

Thomopoulos S., Das R., Silva M.J., Sakiyama-Elbert S., Harwood F.L., Zampiakis E., et al., 2009, Enhanced Flexor Tendon Healing through Controlled Delivery of PDGF-BB, Journal of Orthopaedic Research, p. 1209-1215.

* cited by examiner

D-D

DEVICE FOR REPAIR SURGERY OF CYLINDRICAL ORGANS, PARTICULARLY RUPTURED TENDONS

This application claim priority from PCT application No. PCT/EP2012/066564 filed Aug. 26,2012 which claims priory from European application No. EP 11178917.8 filed on Aug. 25, 2011, the disclosures of which are incorporated herein by reference.

FIELD OF THE INVENTION

The present invention relates to a device for repair surgery of cylindrical organs, particularly ruptured tendons. It further relates to a kit for tendon repair surgery, to a composition for promoting tendon regrowth after tendon repair surgery, and to a method for repair surgery of a ruptured cylindrical organ, particularly a ruptured tendon.

BACKGROUND OF THE INVENTION

In spite of continuous progress in the field of (flexor) tendon rupture repair, there are still open problems up-to-date. In particular, adhesion and rupture in the early healing phase with a reoperation rate of 7 to 15% lead to substantial work disability and costs. On the one hand side, the repaired tendons should have high primary repair strength for early active post-operative motion, and on the other hand side, the repair site should be flat in order to allow the tendon to glide smoothly in the tendon sheath (Buschmann et al. 2011). According to Kuwata et al., optimum primary repair strength requires multi-strand locking loops and cross-stitch epitendinous sutures (Kuwata et al. 2007). However, such repair techniques lead to bulging at the repair site and thus to adhesion during the healing process (Khanna et al. 2009). Although tricks such as locating the knots between the locking loops or burying them between the tendon stumps instead of placing them outside on the tendon surface may help in reducing potential adhesion formation, such procedures often have only small impacts with respect to anti-adhesion or unhindered gliding (Komatsu et al. 2007). In the past, different interposition techniques with artificial materials could not positively affect the outcome.

SUMMARY OF THE INVENTION

In view of the above, it is an object of the present invention to provide an improved device for repair surgery of cylindrical organs, particularly ruptured tendons. Further objects of the invention are to provide an improved kit for tendon repair surgery, an improved composition for promoting tendon regrowth after tendon repair surgery, and an improved method for repair surgery of a ruptured cylindrical organ, particularly a ruptured tendon.

These objects are achieved by the device, the kit, the composition and the method defined in the respective independent claims.

Advantageous embodiments of the invention are defined in the dependent claims.

According to a first aspect of the present invention, there is provided a device for repair surgery of cylindrical organs, which is configured as a tubular sheath made of a biocompatible and biodegradable polymer. The tubular sheath comprises an elastic fiber mesh formed by electrospinning of said polymer, and has an inner wall surface and an outer wall surface substantially parallel thereto, meaning that the wall thickness is substantially constant. One of the wall surfaces is comparatively rough whereas the other one of the wall surfaces is comparatively smooth, and the tubular sheath has a Young elasticity modulus of about 2 to about 15 MPa and an elongation at break of about 50 to about 1,000%.

While it is contemplated that the device may be used for repair surgery of a whole variety of cylindrical organs such as nerves, blood vessels and certain muscles, it is particularly useful for repair surgery of ruptured tendons. In the present context the term "cylindrical" shall be understood as "having substantially cylindrical symmetry" in line with the fact that human and animal organs do not exhibit perfect cylindricity in the geometrical sense both because of inherent slight irregularities of their shape and because of their deformability.

The terms "biocompatible" and "biodegradable" are generally known in the field of surgery. Synthetic biocompatible and bioresorbable polymers are becoming increasingly popular for surgical applications either as tissue engineered artificial grafts and/ or as bioactive carrier devices delivering growth factors (Costa et al. 2006), cytokines and other bioactive substances (Maurus et al. 2006; Corsi et al. 2007; Bullough et al. 2008). Tendon grafts can also be seeded with stem cells improving the early healing process (Chong et al. 2007). The advantage of such polymers is that their mechanical properties as well as their degradation rates can be controlled and adjusted for specific medical applications (Saad et al. 1999; Durselen et al. 2001; Milleret et al. 2009; Sahoo et al. 2010). Moreover, tissue integration can be regulated by porosity and architecture of the material used for grafting (Henry et al. 2009).

The technique of forming a tubular sheath comprising an elastic polymeric fiber mesh by electrospinning is generally known (see, e.g. US 2011/0039101 A1). As the fiber mesh is formed on a cylindrical or conical target with a smooth surface, the resulting sheath has a comparatively smooth surface on its inner wall adjacent the target and a comparatively rough outer surface on its outer wall. For example, the smooth surface will have a dynamic friction coefficient of about 0.85 whereas the rough surface will have a dynamic friction coefficient of about 1.05. As will be explained in more detail further below, this difference in surface roughness can be exploited in repair surgery by first everting the tubular sheath so as to have the rough surface as the inner wall. This allows for firm contact of the sheath with the cylindrical organ to be repaired and reduces the friction between the outer wall and any surrounding tissue, thereby improving mobility of the repaired organ, for example gliding of a tendon in the tendon sheats.

By having a Young elasticity modulus of about 2 to about 15 MPa and an elongation at break of about 50 to about 1,000%, the tubular sheath can be readily expanded when being placed on the repaired region and it can subsequently provide a long lasting radially inward directed pressure that contributes to an improved healing process.

According to an advantageous embodiment, the polymer constituting the tubular mesh is a biodegradable polyester urethane block copolymer with poly-hydroxy-butyrate as a hard segment and $\epsilon$-caprolactone as a soft segment. Such polymers are known and can be purchased as DegraPol® from ab medica s.p.a., Via Nerviano, 31, 20020 Lainate (MI) Italy. Degrapol has been shown to be biocompatible for fibroblasts, osteoblasts and tenocytes in vitro; moreover, it is biodegradable as well as cyto- and hemocompatible (Saad et al. 1998; Sukthankar 1999; Milleret et al. 2009). The degradation rate can be adjusted in the range from a few weeks up to a few years.

However, a particularly preferred embodiment involves a specifically selected type of the above mentioned polyester urethane block copolymer, characterized by a soft segment with an average molecular weight of about 950 g/mol to about 1,200 g/mol, a relative content of said soft segment of about 70 to about 75 parts by weight and a relative content of said hard segment of about 25 to about 30 parts by weight. The term "relative content" is used here because, as will be generally known, formation of such block copolymers further requires the addition of an appropriate coupling agent. In the present case, this is an isocyanate coupler. If not specifically mentioned otherwise, average molecular weights reported here are number averaged molecular weights $M_n$, which can be determined e.g. by means of gel permeation chromatography (GPC).

With this specifically selected polymer, the tubular sheath has substantially improved mechanical properties, namely, a Young elasticity modulus of about 2 to about 4 MPa, particularly about 2.8 to about 3.2 MPa while still having an elongation at break of about 500 to about 1,000%, particularly about 500 to about 600%.

As already pointed out further above, the device of the present invention is generally intended for repair surgery of organs with substantially cylindrical symmetry. This also includes configurations with variable diameter. Therefore, according to one embodiment the tubular sheath is of substantially frustoconical shape, i.e. it has a diameter that monotonously decreases in one axial direction. Typically, the half-aperture angle, i.e. the angle between the wall surface and the longitudinal axis will be in the range of about 1 to about 10°. However, the useful tubular shapes also include configurations with a nonlinear diameter variation, i.e. having a curved longitudinal section. The specific shape will be selected according to the shape of the organ to be repaired. As will be understood, the manufacture of tubular sheaths with such specific shapes by electrospinning is readily achieved by selecting an appropriately formed deposition target.

Without being bound by theory, it appears that a beneficial influence on the healing process after repair surgery is due to a stimulating effect caused by the mechanical pressure generated from the elastic tubular sheath.

In a further embodiment, the tubular sheath further comprises at least one therapeutic agent for stimulating tendon regrowth processes. The application of bioactive substances that can stimulate the healing process in situ is generally known (Ehrbar et al. 2007). If such factors and substances are linked to a suitable carrier device delivering them to the repair site in appropriate concentrations and under controlled release kinetics, the healing of lacerated tissue can be accelerated. In particular, such therapeutic agent can be selected from the group consisting of growth hormones, growth factors, pharmaceutical agents and growth promoting cells, including stem cells.

In a particularly advantageous embodiment, the fiber mesh forming the tubular sheath comprises hollow fibers containing at least one appropriate therapeutic agent. When the fiber material slowly decomposes, typically on a time scale of a few weeks, the therapeutic agent contained therein is gradually released and delivered to the repaired organ region.

According to a further aspect of the present invention, a kit for tendon repair surgery comprises at least one device as defined above and having a nominal inner tube diameter d1. The kit further comprises an application tool configured as a pair of tweezers with resilient members, each member having a free end and a joined end, with the respective joined ends mutually connected to each other. The free ends are formed with rounded tips for easier insertion into a tubular sheath and for prevention of any damage to the organ onto which the sheath will be applied by means of the tool. The resilient members are biased in such manner as to establish a first distance s1 between their free ends when no force is applied to the members. By virtue of the fact that the first distance s1, i.e. the separation distance of the tweezer ends at rest is larger than the inner tube diameter d1, it is necessary to push together the tweezer members in a closing movement in order to be able to slide their ends into the tubular device. Upon release, the tweezer members undergo an opening movement driving their ends apart and thereby expand the diameter of the tubular device, thus facilitating its application over the end of a ruptured organ segment. It will be understood that the application tool shall be made of a material that is suitable for surgical environments.

According to a further aspect of the present invention, there is provided a composition for promoting tendon regrowth after tendon repair surgery. Such composition comprises a biodegradable polyester urethane block copolymer with poly-hydroxy-butyrate as a hard segment and ε-caprolactone as a soft segment, for promoting tendon regrowth after tendon repair surgery. As already mentioned further above, this polymer can be purchased as DegraPol®.

Advantageously, the above mentioned polyester urethane block copolymer is characterized by a soft segment with an average molecular weight of about 950 g/mol to about 1,200 g/mol, a relative content of said soft segment of about 70 to about 75 parts by weight and a relative content of said hard segment of about 25 to about 30 parts by weight. In a particularly preferred embodiment, the composition further comprises at least one therapeutic agent for stimulating tendon regrowth processes.

According to still another aspect of the invention, there is provided a method for repair surgery of a ruptured cylindrical organ, particularly a ruptured tendon, comprising the steps of:
a) selecting a tubular segment of a device as defined above, said tubular segment having a nominal inner tube diameter d1 smaller than an outer diameter d2 of a pair of ruptured organ ends;
b) arranging said tubular segment so that said comparatively rough wall surface forms said inner wall surface;
c) expanding said tubular segment to a diameter larger than said outer ruptured organ diameter d2 and sliding said tubular segment over one of said ruptured organ ends;
d) surgically rejoining said ruptured organ ends, thereby forming a rejoined organ region;
e) re-expanding said tubular segment to a diameter larger than said outer ruptured organ diameter d2 and sliding said tubular segment over said rejoined organ region;
f) allowing healing of said rejoined organ region under a radially inward pressure exerted by said tubular segment.

In a preferred embodiment, the above defined method is applied for repair surgery of a ruptured tendon.

BRIEF DESCRIPTION OF THE DRAWINGS

The above mentioned and other features and objects of this invention and the manner of achieving them will become more apparent and this invention itself will be better understood by reference to the following description of various embodiments of this invention taken in conjunction with the accompanying drawings, wherein.

DETAILED DESCRIPTION OF THE INVENTION

Figure 1:
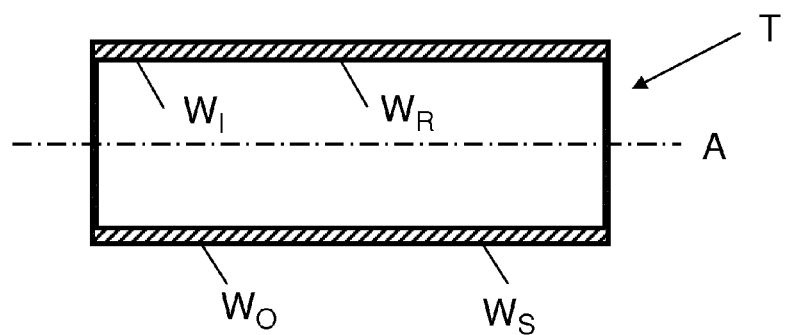
FIG. 1 shows a first embodiment of a device for repair surgery, in a longitudinal cross-section.

The device for repair surgery of cylindrical organs, particularly ruptured tendons, as shown in FIG. 1 is configured as a tubular sheath T made of a biocompatible and biodegradable polymer. The tubular sheath T is approximately cylindrically shaped along a longitudinal axis A. It comprises an elastic fiber mesh formed by electrospinning of said polymer and has an inner wall surface $W_I$ and an outer wall surface $W_O$ substantially parallel thereto. One of said wall surfaces—in the presently shown case it is the inner wall surface $W_I$—is comparatively rough $W_R$ whereas the other one of said wall surfaces—in the presently shown case it is the outer wall surface $W_O$—is comparatively smooth $W_S$. The configuration shown in FIG. 1 is the one to be used for the intended surgical application. As explained further above, this configuration is obtained from a freshly produced electrospun tubular sheath by everting the same, i.e. by switching the inner and outer side thereof.

Figure 2:
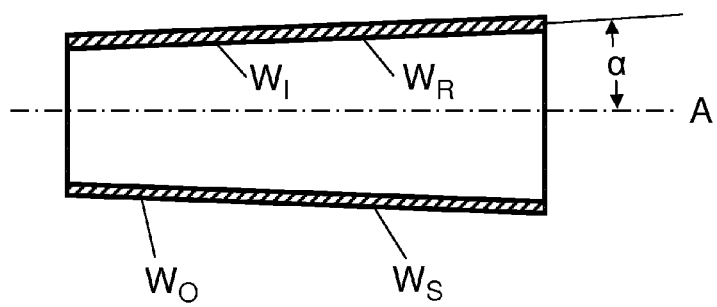
FIG. 2 shows a further embodiment of a device for repair surgery, in a longitudinal cross-section.

FIG. 2 shows a further embodiment wherein the tubular sheath is of substantially frustoconical shape having a substantial half-aperture angle, i.e. an angle α between the wall surface and the longitudinal axis A. Depending on the organ to be operated, α will be in the range of about 1° to about 10°.

FIG. 3 shows a kit for tendon repair surgery comprising a section of a tubular sheath device T as defined further above and having a nominal inner tube diameter d1. The kit further comprises an application tool configured as a pair of tweezers with resilient members m1 and m2, each member having a free end f1 or f2, respectively, and a joined end. The joined ends, which are not shown in the figures, are mutually connected to each other. The free ends f1 and f2 are formed with rounded tip regions so as to facilitate insertion into the tubular sheath and to avoid any injury to the tendon or other organ onto which the sheath will be applied. As seen particularly from FIG. 3d, the members are shaped liked longitudinal half sections of a hollow tube, which is particularly adapted to the intended use. The resilient members are biased in such manner as to establish a first distance s1 between their free ends when no force is applied to the members. Importantly, the first distance s1, i.e. the separation distance of the tweezer ends at rest is larger than the inner tube diameter d1; as shown in FIG. 3a, the distance s1 is measured between the two outer faces of the tweezer ends f1 and f2. This mechanical biasing can be achieved either by using an inherently elastic material and/or by inserting an appropriate spring element in the region between the two members.

Figure 3A:
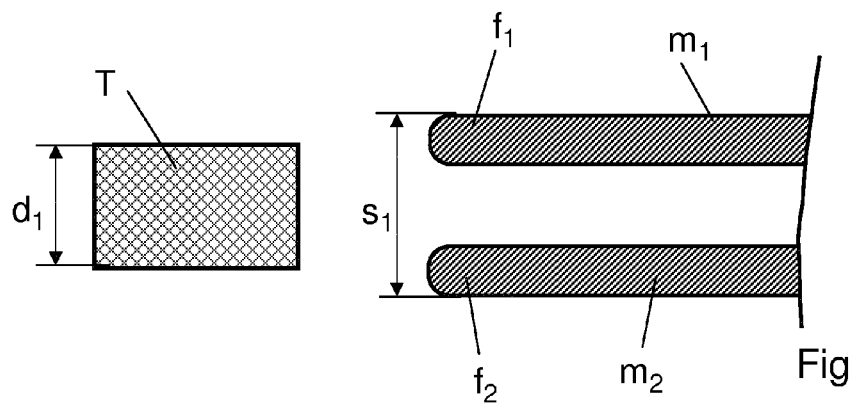
FIG. 3 shows a kit for tendon repair surgery, (a) to (c) in three different positions, in a schematic representation, and (d) in a sectional view according to section D-D of FIG. 3c.
Figure 3B:
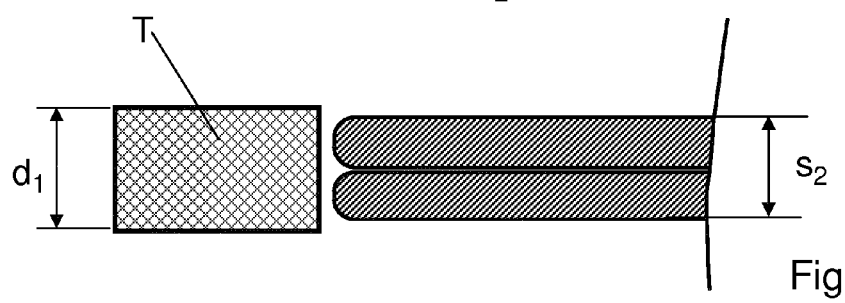
Figure 3D:
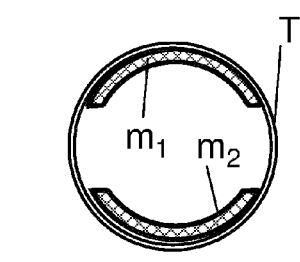
Figure 3C:
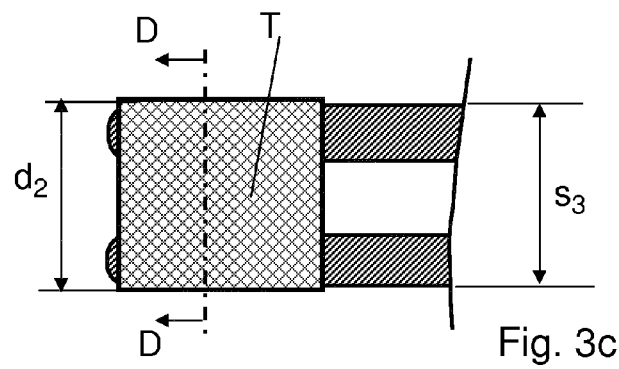

By pushing together the tweezer members in a closing movement, the distance between their free ends is reduced to a value s2 that is smaller than the sheath diameter d1, as shown in FIG. 3b. In is then possible to slide the tweezer ends into the tubular device T. By reducing the force applied to the tweezer members their resilience causes an opening movement driving their ends apart to a separation distance s3 that is larger than s2. This causes an expansion of the tubular device so as to reach a nominal inner diameter d2 which is essentially identical to the separation distance s3, as shown in FIG. 3c. The expanded tubular sheath device can then be applied over the end of a ruptured organ segment; the tweezer tool is then retracted so as to leave the sheath device in place.

EXAMPLE 1

Materials and Methods
Polymer

A biodegradable polyester urethane polymer (trade name DegraPol®, henceforth abbreviated as "DP") with poly-hydroxy-butyrate as a crystalline segment and ε-caprolactone as a soft segment was produced according to given protocols (Lendlein et al. 1998; Lendlein et al. 2000; Milleret et al. 2009).
Scaffold Fabrication The electrospinning setup was assembled in-house and consisted of a syringe pump (Racel Scientific Instruments Inc., USA), a spinning head consisting of a central stainless steel tube (1 mm inner diameter and 0.3 mm wall thickness, Angst & Pfister AG, Switzerland), a cylindrical rotating aluminum mandrel for fiber collection (length: 100 mm, diameter: 4 mm) and a DC high voltage supply (Glassman High Voltage Inc., USA). A 25 wt % solution of the DegraPol® (DP) in chloroform (Fluka, puriss.) was prepared by dissolving the polymer under stirring overnight. Electrospinning voltage (15 kV) was applied with a high voltage supply between a needle and the rotating cylindrical collector (20 cm apart from each other). As-spun tubes were removed from the target by slightly swelling them with ethanol (Fluka, puriss.) and then dried under vacuum at room temperature.
Scaffold Characterization The polymer density $\rho_0$ was determined according to Simonet et al. and was 1.15 g/cm³ (Simonet et al. 2007). The bulk densities p of the electrospun polymers were determined gravimetrically using the weights of precisely cut samples of defined area and thickness. The scaffold dimensions were measured using SEM micrographs of the scaffold. The overall mesh porosity P was calculated according to the following expression:

$$P = \left(1 - \frac{\rho_0}{\rho}\right) \times 100 \ [\%]$$

Figure 4A:
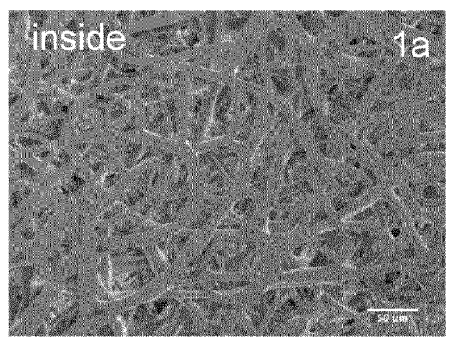
FIG. 4 shows SEM images of electrospun Degrapol tubes; (a) inside, (b) outside and in a (c) cross-sectional view.
Figure 4B:
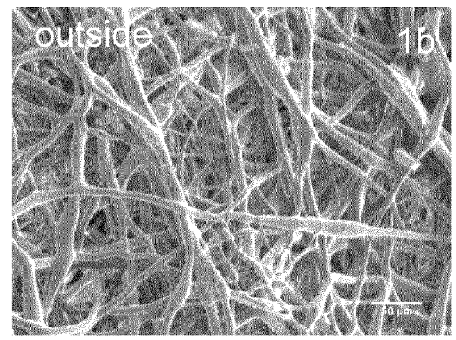
Figure 4C:
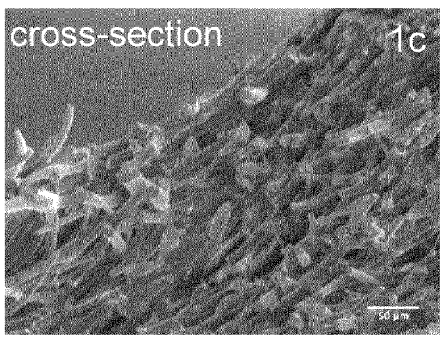

The porosity was 75.2±0.7%. The wall thickness was 379.3±18.8 μm as determined by SEM images. As shown in FIGS. 4a to c, the fibers were randomly distributed. Inside the tube the surface was flat (FIG. 4a), whereas outside it was rather rough (FIG. 4b). The cross-section is shown in FIG. 4c.
Animal Study In an exploratory study we implanted DegraPol® tubes produced as described above around transected and conventionally sutured rabbit Achilles tendons and determined their effects 12 weeks post-operatively. Number and morphology of tenocytes, collagen structure and inflammation zones were explored on a histomorphometric basis. Moreover, as we also compared the outcomes of rabbits having one hind leg operated with rabbits having both hind legs operated, which is a systemic burden for the animal, we were able to compare these effects with the ones of the implanted tube. As a consequence, the objectives of this study were (i) to investigate the cellular response in healing rabbit Achilles tendons evoked by implantation of a DegraPol® tube, and (ii) to compare the impacts of one- versus two-hind-leg operated animals on tissue integration and inflammation with the impacts of the application of a DegraPol® tube.

Rabbits

For the in vivo study, eight female New Zealand White rabbits were used (Charles River, Research Models and Services, Germany GmbH, 97633 Sulzfeld, Germany). The range of the weight at the beginning was 2.7 kg-3.2 kg and at the end 3.2 kg-3.8 kg (14 weeks after receipt). All animals were housed in groups and had access to standard pellet diet and water ad libitum. Ethical approval was obtained for the experiments from the veterinary office of Zurich, Switzerland (reference number 92/2009). Prior to surgery, all animals were acclimatized to their environment for two weeks.

Implantation

Before implantation, the DP tubes were sterilized with ethylene oxide at 37° C. The rabbits received premedication with 65 mg/kg body weight Ketamine and 4 mg/kg Xylazine. A venous catheter was inserted in the marginal ear vein. The rabbits were intubated with Propofol i.v. 0.6 mg/ kg-1.3 mg/ kg. Anaesthesia was maintained with 1-2% isofluorane. The hind legs were cleaned with iodine. The Achilles tendon rupture was produced by a paratendineal incision of cutis, subcutis and fascia. The tendon was then sliced perpendicularly to the length of the tendon 2 cm above the calcaneus and one of the two fringed tendon stumps was sutured, while the fiber (USP 4.0 polypropylene) was then pulled through the DP tube, before the second tendon stump was sutured. The fiber was knotted in order to minimize the gap between the stumps. The DP tube was then flipped over the wound. Subsequently the wound was closed with a running suture (using a USP 6.0 polypropylene fiber) of the fascia and interrupted skin. All surgical procedures were performed by the same senior surgeon (MC). Postoperative treatment included a cast having an angle of 60° at the ankle After 3 weeks, the cast was removed and no further device was applied to the hind legs. Twelve weeks post operation, the rabbits were euthanized in deep anaesthesia (100 mg/kg Ketamine and 4 mg/kg Xylazine) with 80 mg/kg Pentobarbital (Esconarkon ad us. vet.). At this time point, DP tubes were degraded by half.

Treatment Groups

The eight rabbits were divided into four groups with two objects each. The first group had one hind leg operated with the application of a conventional four-strand Becker suture (4-str, 1 OP), the other hind leg having no treatment (NT, 1 OP); the second group had one hind leg operated with the application of a conventional four-strand Becker suture and additionally a DP tube (DP, 4-str, 1 OP), the other hind leg having no treatment (NT, 1 OP); the third group had both hind legs operated—one without DP tube (4-str, 2 OP) and one with DP tube (DP, 4-str, 2 OP) and the fourth group received no treatment (NT, 0 OP).

Histological Analyses

After extraction, the Achilles tendon specimens were immediately formalin-fixated. Then, they were dehydrated, paraffin-embedded and sectioned into 3 µm thick slices, one longitudinal section and one cross-section in the DP tube region (perpendicular to the Achilles tendon). After deparaffinizing with xylene and rehydrating the sections (descending gradient of ethanol), they were differently stained: H&E, Hemalaun Sudan, Masson Goldner Trichrome and Picosirius Red according to commonly established procedures.

The H&E-stained longitudinal sections were used to quantify the number of tenocyte nuclei per area at 100× magnification. Six fields of view (FOV) of each object were randomly selected and analyzed with a light microscope (Leica DM 6000 B) equipped with a digital camera. Tenocyte nuclei were dark violet, while tendon tissue was rosy. The same sections were used for evaluation of tenocyte morphology (width of tenocytes) at a 400× magnification. Here, 5 measurements in 3 FOV of each object were analyzed. Moreover, inflammation zones were evaluated in the H&E-stained sections (5 FOV of each object, semi-quantitative analysis), as well as the different cell types: heterophiles or heterocytes (HC; analogous to human sanies-indicating neutrophile granulocytes), macrophages (MP), lympho-cytes (LC), tenoblasts (TB) and tenocytes (TC) in the different reaction zones (5 FOV in each zone of each object). Cell types were distinguished according to their morphology. HC had a lobed nucleus and granules in the cytoplasm; MP had a lot of cytoplasm and a round nucleus; LC had no cytoplasm (just the round nucleus visible), TC had a very flat nucleus, while TB had a thicker nucleus than TC.

The Hemalaun Sudan-stained sections were used to clearly distinguish between DP polymer (red), tendon tissue (grey) and cells (dark blue). Identification of the different reaction zones and determination of the width of these zones was based on Picosirius Red sections. Masson Goldner Trichrome and H&E stained sections were used to analyze the angle of the slightly wavy collagen fibers (green and rosy, respectively). A completely straight fiber would have an angle of 180°. Ten measurements in 2 FOV of each object were evaluated.

Statistical Analysis

The data were analyzed with StatView 5.0.1. One-way analysis of variance (one-way ANOVA) was conducted to test the significance of differences between different surgery methods and between the groups where one hind leg and two hind legs were operated, respectively. Pairwise comparison probabilities (p) were calculated using the Fisher's PLSD post hoc test and, for comparison, the Bonferroni post hoc test. P values<0.05 were considered significant. Values were expressed as means±standard deviations if not otherwise stated. Moreover, to prove equivalency of outcome measures, an equivalency test was performed.

Results

The full results of the above study has been published in a scientific article first made available online on 31 Jan. 2012 (Buschmann et al. 2012, Cellular response of healing tissue to DegraPol tube implantation in rabbit Achilles tendon rupture repair: an in vivo histomorphometric study. *Journal of Tissue Engineering and Regenerative Medicine*). They may be summarized as follows.

Twelve weeks after operation, we clearly found that the implanted tube had no adverse effects on the repaired tendon tissue on a histomorphometric basis. We found statistically proven equivalency for tenocyte density, tenocyte morphology and number of inflammation zones whether a DP tube was implanted or not. These findings are a prerequisite for using it as a carrier system. As a matter of fact, it has been shown in different studies that factors such as IGF-1, PDGF-BB, β-FGF, rhBMP-12 and BMP-13 accelerate and support tendon healing (Costa et al. 2006; Rodeo et al. 2007; Bullough et al. 2008; Seeherman et al. 2008; Thomopoulos et al. 2009). Hyaluronic acid gel has as well been reported to accelerate tendon healing (de Wit et al. 2009). Such stimulating factors could be adsorbed or chemically linked to DP tubes which they then deliver in situ to the repair site as has been shown for BMP and for biopharmaceuticals linked to hydrogels (Ehrbar et al. 2008; Hanseler et al. 2010; Jo et al. 2010). Another advantage of applying a tube around the repair site is that the tube could be coated with different factors inside and/or outside, which allows supporting the healing of the tendon tissue inside and the gliding in the intrasynovial sheath outside.

Besides the statistical equivalency for tenocyte density, morphology and number of inflammation zones, the only statistically significant difference between DP treated and conventionally sutured tendons was observed for the collagen structure. During the healing process, collagen fibers go through different stages of order. At the beginning, the fibers are quite randomly distributed, while during the remodeling stage (at weeks 6 to 10), collagen fibers become aligned with the direction of stress (Sharma and Maffulli 2006). The slightly wavier collagen fibers we observed for the DP treated specimen with 5-10° smaller angles may be due to a little retarded healing process or caused by shifting the burden during hopping to the healthy leg and thereby relieving the treated leg.

In addition, we evaluated the inflammation zones in the healing tendon tissue either at least 1 mm away from the implant or in the implant with the integrated new tissue. Obviously, we found four times higher cell densities in inflammation zones compared to healthy tissue. Macrophages were the predominant cell type in the inflammation zone. A rather unexpected result was that the number of macrophages found in the inflammation zones that were at least 1 mm away from the implant was significantly higher compared to the reactive zones of the DP area where predominantly tenocytes moved into the implant material. Thus, the small trauma caused by stitching evoked a clear inflammatory cell response while the foreign DP body did not elicit such a reaction. Neither was the amount of heterocytes high in the DP treated area. Heterocytes are typically produced in sanies extruding wounds. Only lymphocytes were found to be up to 25% of the total cell number, but this was restricted to one special area of the DP tube, namely an area where the polymer had already degraded to an advanced stage. In this zone with slightly elevated lymphocyte density, we observed very small droplets that probably are tri- or tetramers of the polyester-urethane which are not water-soluble. When observing these small droplets for the first time we interpreted them as intruding bacteria, but Brown Brenn Gram staining clearly showed that these were neither Gram-positive nor Gram-negative bacteria.

With regard to the 3R principle (Russel and Burch 1959), we performed animal experiments where one hind leg or both hind legs of the rabbits were operated and compared the outcomes. If 2-leg operated animals behaved the same as 1-leg operated ones, then the number of rabbits could be reduced by half in further experiments of this kind Moreover, such experiments enabled us to compare the effects of a DP implantation with the effects of a systemic burden caused by a 2-leg operation. Comparing the 1-leg results with the 2-leg results, it turned out that parameters such as tenocyte morphology and collagen structure remained unaffected, while tenocyte density was 17% higher for 1-leg operated animals than for 2-leg operated animals. This was surprising because we hypothesized that more tenocytes would be found in the 2-leg operated animals with the higher systemic burden. This hypothesis arose from the fact that non-treated specimen had a 4-fold lower tenocyte density. It implied that higher burden goes along with higher tenocyte density, which is obviously not the case for the 2-leg operated animals compared to the 1-leg operated ones.

However, as expected the number of inflammation zones was higher in the 2-leg operated specimen. Whereas the inflammation zones were 2.2 fold higher for 1-leg operated animals, they were 3.1 fold higher for the 2-leg operated ones compared to non-treated specimen. This corresponds to a statistically significant difference of 30% more inflammation zones found for the 2-leg operated animals. Compared to the results for DP treated specimen, the influence of a 2-leg operation is much more pronounced with respect to inflammation. DegraPol itself did not show any additional effect, nor for macrophages, heterocytes or lymphocytes, while a 2-leg operated specimen clearly had a higher inflammatory response in the healing tissue. Such increased inflammation may be caused by the 2-leg operated animal's restriction in moving in the early post-op phase when a cast was applied for the first 3 weeks. A 2-leg operated animal with 2 casts is much more restricted in its motion. The 1-leg operated animal still could evade and stress the healthy leg, while the 2-leg operated animal was forced to use both treated hind legs provoking more inflammation reactions.

As a summary and conclusion we could demonstrate that a tight electrospun bioresorbable DP tube can be set around a sutured tendon rupture without any adverse effects. The cellular response of the healing tissue 12 weeks post operation was the same as if no implant was set. Thus, the biodegradable DP polymer tube is a convincing and promising tool and may act as a carrier device for factors that accelerate the intrinsic and extrinsic healing process of the tendon tissue. Additionally, we compared 1-leg operated and 2-leg operated animals and found that inflammation zones were significantly higher in the 2-leg operated case. Overall, a 2-leg operation seems to be a burden for the animal, while a DP implant does not affect any parameters concerning tenocytes, collagen and inflammation, which makes it a promising carrier system in the future.

EXAMPLE 2

One major problem during tendon healing is the formation of adhesions to the surrounding tissue. To study a possible protective effect by the application of a DP tube, a further series of experiments was conducted in which twelve New Zealand white rabbits received a clean-cut Achilles tendon laceration and were repaired with a 4-strand suture. Six rabbits got additionally a tight DP tube at the repair site. Tendons were analysed by static and dynamic ultrasound and power Doppler ultrasound (control: healthy contralateral legs). The ultrasound outcome was correlated to the tendon shape, tenocyte and tenoblast density, tenocyte and tenoblast nuclei width, collagen fibre orientation and adhesion extent. All repaired tendons showed a spindle-like morphology in the ultrasound, corresponding to the same shape caused by the swollen epitenon (histology). Prediction of adhesion formation by dynamic ultrasound assessment was confirmed by determining the contact region of the newly formed tissue to the surrounding tissue (histology). Importantly, both at three weeks post-operation and at six weeks post-operation the DP tube treated specimen showed significantly less adhesion formation compared to merely 4-strand sutured.

EXAMPLE 3

In order to make the established and widely tested DP polymer (from now on called "classic DP") softer, more elastic and hence more suitable for the purpose of tendon rupture repair, the synthesis was slightly modified and adapted to obtain what will be called "new DegraPol" or "new DP".

Briefly, for the synthesis of the block copolymer, 40 wt % (classic DP) or 25 wt % (new DP) of poly(3-(R)-hydroxybutyrate)-co-(ε-caprolactone)-diol $M_n$=2660 g mol$^{-1}$ (classic DP) and $M_n$=2824 g mol$^{-1}$ (new DP) and 60 wt % with $M_n$=1250 g mol$^{-1}$ (classic DP) or 75 wt % with $M_n$=1000 g mol$^{-1}$ (new DP) poly(ε-caprolactone)-diol-co-glycolide (15 mol % glycolide 85 mol % ε-caprolactone) were dissolved in 1.4-dioxane and dried by heating and refluxing the solvent over molecular sieves (pore size 0.4 nm) situated in a Soxhlet apparatus mounted onto the reaction vessel, until the water content was below 20 ppm. The reaction mixture was cooled to 83° C. before the stochiometric amount, with respect to the two diols, of 2,2,4-trimethylhexane-diisocyanate (TMDI) was added. After about one day of reaction, three portions dibutyltin dilaurate (20 ppm) were added within 1 day in order to reach molecular weights between 60 and 110 kDa (for classic and new DP, respectively). The polymer was precipitated in dry ice cooled hexane isomers and subsequently purified via dissolution in chloroform and filtration over a silicagel 60 (Fluka) column. A second precipitation in cooled ethanol ended the process.

The mechanical properties such as Young modulus and elongation at break were obtained from stress/strain curves measured at room temperature using a uniaxial load test machine (Instron tensile tester, model 5864) at a crosshead speed of 12.6 mm min$^{-1}$ using a sample gauge length of 12.6 mm (100% min$^{-1}$). Each sample was measured in triplicates.

The coefficient of sliding friction was determined for the initially inner (flat) surface and the outer (rough) surface of the electrospun tubes. The tubes were cut with a scalpel in order to obtain a rectangular piece of material. The piece was fixed on a flat polished Delrin® cube and loaded with a 50 g weight, resulting in a mass (m) of 59.16±0.2 g. At a constant velocity of 5.6±0.3 cm s$^{-1}$, the object was pulled over an endlessly rolling plastic surface (self-made machine) and the tensile force, $F_t$(N), was measured (n=3). The coefficient of sliding friction (μ) was calculated according 1 to the following expression, wherein g=9.81 m s$^{-2}$:

$$\mu = \frac{F_t}{m \cdot g}$$

The properties of the new DP material were compared with the ones of the classic DP. Both films and electrospun materials were compared and showed to have diverse characteristics which are caused by the secondary structure of the fibres in the electrospun material. As can be seen in the Table, the Young Modulus of the new DP film was much smaller compared to the Young modulus of the classic DP film. In addition, the elongation at break of the new DP film was around half the one of the classic DP film. For the electrospun materials, the SEM images of the classic and new DP material were similar. Only the homogeneity of the fibre diameter differed with 10±7 μm for the classic DP and 10±3 μm for the new DP material. The Young Modulus of the new electrospun DP was 4 times smaller as for the classic electrospun DP. However, in contrast to the films, the new electrospun DP had a 9-fold higher elongation at break compared to the classic electrospun DP.

TABLE

Material properties: Young modulus and elongation at break for films and electrospun tubes based on classic and new DP material (n = 3):

|  | Classic DegraPol | New DegraPol |
|---|---|---|
| Young Modulus of films [MPa] | 45.2 ± 8.9 | 6.0 ± 0.9 |
| Elongation at break of films [%] | 555.2 ± 76.2 | 276.5 ± 51.3 |
| Young Modulus of electrospun tubes [MPa] | 12.96 ± 2.78 | 3.03 ± 0.17 |
| Elongation at break of electrospun tubes [%] | 61.33 ± 11.37 | 544.00 ± 67.88 |

The coefficients of sliding friction of the electrospun DP surfaces were measured on an endlessly rolling plastic surface. Polished Delrin® (polyoxymethylen) was used as a reference material. For polished Delrin®, the coefficient of sliding friction was 0.478±0.034. The rough surface of the electrospun DP tubes had a sliding friction coefficient of 1.035±0.086, while it was 0.862±0.086 for the flat surface of the tube (p=0.0278, significantly different in the Fisher's PLSD post hoc test, not significantly different in the Bonferroni post hoc test; only for p<0.0167).

In accordance with the findings for the classic DP material, the application of the new DP does not in any way disturb the healing process of the ruptured tendon.

References

Bullough R, Finnigan T, Kay A, Maffulli N and Forsyth N R 2008, Tendon repair though stem cell intervention: Cellular and molecular approaches. *Disability and Rehabilitation*, 30(20-22), 1746-1751

Buschmann J, Müller A, Feldman K, Tervoort T A, Fessel G, Snedeker J G, et al. 2011, Small Hook Thread (Quill) and Soft Felt Internal Splint to Increase the Primary Repair Strength of Lacerated Rabbit Achilles Tendons: Biomechanical Analysis and Considerations for Hand Surgery. *Clinical Biomechanics*, 26(6), 626-631

Chong A K S, Ang A D, Goh J C H, Hui J H P, Lim A Y T, Lee E H, et al. 2007, Bone marrow-derived mesenchymal stem cells influence early tendon-healing in a rabbit Achilles tendon model. *Journal of Bone and Joint Surgery-American Volume*, 89A(1), 74-81

Corsi K A, Schwarz E M, Mooney D J and Huard J 2007, Regenerative medicine in orthopaedic surgery. *Journal of Orthopaedic Research*, 25(10), 1261-1268

Costa M A, Wu C, Pham B V, Chong A K S, Pham H M and Chang J 2006, Tissue engineering of flexor tendons: Optimization of tenocyte proliferation using growth factor supplementation. *Tissue Engineering*, 12(7), 1937-1943 de Wit T, de Putter D, Tra W M W, Rakhorst H A, van Osch G, Hovius S E R, et al. 2009, Auto-Crosslinked Hyaluronic Acid Gel Accelerates Healing of Rabbit Flexor Tendons In Vivo. *Journal of Orthopaedic Research*, 27(3), 408-415

Durselen L, Dauner M, Hierlemann H, Planck H, Claes L E and Ignatius A 2001, Resorbable polymer fibers for ligament augmentation. *Journal of Biomedical Materials Research*, 58(6), 666-672

Ehrbar M, Rizzi S C, Hlushchuk R, Djonov V, Zisch A H, Hubbell J A, et al. 2007, Enzymatic formation of modular cell-instructive fibrin analogs for tissue engineering. *Biomaterials*, 28(26), 3856-3866

Ehrbar M, Schoenmakers R, Christen E H, Fussenegger M and Weber W 2008, Drug-sensing hydrogels for the inducible release of biopharmaceuticals. *Nature Materials*, 7(10), 800-804

Hanseler P, Ehrbar M, Jung U W, Jung R, Hammerle C and Weber F 2010, Bone Morphogenetic Protein-2-Adsorption and Release Behaviour on Clinically Relevant Materials. *Bone*, 46108

Henry J A, Burugapalli K, Neuenschwander P and Pandit A 2009, Structural variants of biodegradable polyesterurethane in vivo evoke a cellular and angiogenic response that is dictated by architecture. *Acta Biomaterialia*, 5(1), 29-42

Jo Y S, Rizzi S C, Ehrbar M, Weber F E, Hubbel J A and Lutolf M P 2010, Biomimetic PEG hydrogels crosslinked with minimal plasmin-sensitive tri-amino acid peptides. *Journal of Biomedical Materials Research Part A*, 93A(3), 870-877

Khanna A, Friel M, Gougoulias N, Longo U G and Maffulli N 2009, Prevention of adhesions in surgery of the flexor tendons of the hand: what is the evidence? *British Medical Bulletin*, 9085-109

Komatsu F, Mori R, Uchio Y and Hatanaka H 2007, Optimum location of knot for tendon surgery in side-locking loop technique. *Clinical Biomechanics*, 22(1), 112-119

Kuwata S, Mori R, Yotsumoto T and Uchio Y 2007, Flexor tendon repair using the two-strand side-locking loop technique to tolerate aggressive active mobilization immediately after surgery. *Clinical Biomechanics*, 22(10), 1083-1087

Lendlein A, Neuenschwander P and Suter U W 1998, Tissue-compatible multiblock copolymers for medical applications, controllable in degradation rate and mechanical properties. *Macromolecular Chemistry and Physics*, 199 (12), 2785-2796

Lendlein A, Neuenschwander P and Suter U W 2000, Hydroxy-telechelic copolyesters with well defined sequence structure through ring-opening polymerization. *Macromolecular Chemistry and Physics*, 201(11), 1067-1076

Maurus C F, Schneider M K J, Schmidt D, Zund G and Seebach J D 2006, Activation of human microvascular endothelial cells with TNF-alpha and hypoxia/reoxygenation enhances NK-cell adhesion, but not NK-cytotoxicity. *Transplantation*, 81(8), 1204-1211

Milleret V, Simonet M, Bittermann A G, Neuenschwander P and Hall H 2009, Cyto- and Hemocompatibility of a Biodegradable 3D-Scaffold Material Designed for Medical Applications. *Journal of Biomedical Materials Research Part B-Applied Biomaterials*, 91B(1), 109-121

Rodeo S A, Potter H G, Kawamura S, Turner A S, Kim H J and Atkinson B L 2007, Biologic augmentation of rotator cuff tendon-healing with use of a mixture of osteoinductive growth factors. *Journal of Bone and Joint Surgery-American Volume*, 89A(11), 2485-2497

Russel W M S and Burch R L (1959). The principle of humane experimental technique. London, Universities Federation for Animal Welfare.

Saad B, Kuboki Y, Welti M, Uhlschmid G K, Neuenschwander P and Suter U W (1999). DegraPol-Foam: A degradable and highly porous polyesterurethane foam as a new substrate for bone formation. 12th World Congress of the International-Society-for-Artificial-Organs/26th Congress of the European-Society-for-Artificial-Organs, Edinburgh, Scotland, Blackwell Science Inc.

Sahoo S, Toh S L and Goh J C H 2010, PLGA nanofiber-coated silk microfibrous scaffold for connective tissue engineering. *Journal of Biomedical Materials Research Part B-Applied Biomaterials*, 95B(1), 19-28

Seeherman H J, Archambault J M, Rodeo S A, Turner A S, D'Augusta D, Li X J, et al. 2008, rhBMP-12 Accelerates Healing of Rotator Cuff Repairs in a Sheep Model. *Journal of Bone and Joint Surgery-American Volume*, 90A(10), 2206-2219

Sharma P and Maffulli N 2006, Biology of tendon injury: healing, modeling and remodeling. *Journal of Musculoskeletal Neuronal Interaction*, 6(2), 181-190

Simonet M, Schneider O D, Neuenschwander P and Stark W J 2007, Ultraporous 3D polymer meshes by low-temperature electrospinning: Use of ice crystals as a removable void template. *Polymer Engineering and Science*, 47(12), 2020-2026

Thomopoulos S, Das R, Silva M J, Sakiyama-Elbert S, Harwood F L, Zampiakis E, et al. 2009, Enhanced Flexor Tendon Healing through Controlled Delivery of PDGF-BB. *Journal of Orthopaedic Research*, 27(9), 1209-1215

The invention claimed is:

1. A device for repair surgery of ruptured tendons, configured as a tubular sheath (T) made of a biocompatible and biodegradable polymer, characterized in that said tubular sheath comprises an elastic fiber mesh formed by electrospinning of said polymer, said tubular sheath having an inner wall surface and an outer wall surface substantially parallel thereto, wherein one of said wall surfaces is comparatively rough ($W_R$) and the other one of said wall surfaces is comparatively smooth ($W_s$), said tubular sheath having a Young elasticity modulus circumferentially of 2 to 4 MPa and an elongation at break of 500 to 1000%, wherein said polymer is a biodegradable polyester urethane block copolymer with poly-hydroxy-butyrate as a hard segment and c-caprolactone as a soft segment, characterized in that said soft segment has an average molecular weight of 950 g/mol to 1,200 g/mol and wherein the relative content of said soft segment is 70 to 75 parts by weight whereas the relative content of said hard segment is 25 to 30 parts by weight.

2. The device according to claim 1, wherein said tubular sheath has a Young elasticity modulus of 2.8 to 3.2 MPa and an elongation at break of 500 to 600%.

3. The device according to claim 1, wherein said tubular sheath is of substantially frustoconical shape.

4. The device according to claim 1, wherein said tubular sheath further comprises at least one therapeutic agent for stimulating tendon regrowth processes.

5. The device according to claim 4, wherein said therapeutic agent is selected from the group consisting of growth hormones, pharmaceutical agents and growth promoting cells, including stem cells.

6. The device according to claim 4, wherein said fiber mesh comprises hollow fibers containing said therapeutic agent(s).

7. A kit for tendon repair surgery comprising at least one device as defined in claim 1 and having a nominal inner tube diameter d1, the kit further comprising an application tool, said tool being configured as a pair of tweezers having resilient members each one having a free end and a joined end, said joined ends being mutually connected, said free ends being formed with rounded tips, said resilient members being biased in such manner as to establish a first distance s1 between said free ends when no force is applied to said members, said first distance s1 being larger than said inner tube diameter d1.

8. A method for repair surgery of a ruptured tendon, comprising steps of a) selecting a tubular segment of a device configured as a tubular sheath (T) made of a biocompatible and biodegradable polymer, characterized in that said tubular sheath comprises an elastic fiber mesh formed by electrospinning of said polymer, said tubular sheath having an inner wall surface and an outer wall surface substantially parallel thereto, wherein one of said wall surfaces is comparatively rough ($W_R$) and the other one of said wall surfaces is comparatively smooth ($W_s$), said tubular sheath having a Young elasticity modulus circumferentially of 2 to 4 MPa and an elongation at break of 500 to 1000%, wherein said polymer is a biodegradable polyester urethane block copolymer with poly-hydroxy-butyrate as a hard segment and c-caprolactone as a soft segment, characterized in that said soft segment has an average molecular weight of 950 g/mol to 1,200 g/mol and wherein the relative content of said soft segment is 70 to 75 parts by weight whereas the relative content of said hard segment is 25 to 30 parts by weight said tubular segment having a nominal inner tube diameter d1 smaller than an outer diameter d2 of a pair of ruptured tendon ends;

b) arranging said tubular segment so that said comparatively rough ($W_R$) wall surface forms said inner wall surface;

c) expanding said tubular segment to a diameter larger than said outer ruptured tendon diameter d2 and sliding said tubular segment over one of said ruptured tendon ends;

d) surgically rejoining said ruptured tendon ends, thereby forming a rejoined tendon region;

e) re-expanding said tubular segment to a diameter larger than said outer ruptured tendon diameter d2 and sliding said tubular segment over said rejoined tendon region; and, f) allowing healing of said rejoined tendon region under a radially inward pressure exerted by said tubular segment.

9. The device according to claim 5, wherein said fiber mesh comprises hollow fibers containing said therapeutic agent(s).

10. A kit for tendon repair surgery comprising at least one device as defined in claim 2 and having a nominal inner tube diameter d1, the kit further comprising an application tool, said tool being configured as a pair of tweezers having resilient members each one having a free end and a joined end, said joined ends being mutually connected, said free ends being formed with rounded tips, said resilient members being biased in such manner as to establish a first distance s1 between said free ends when no force is applied to said members, said first distance s1 being larger than said inner tube diameter d1.

11. A kit for tendon repair surgery comprising at least one device as defined in claim 3 and having a nominal inner tube diameter d1, the kit further comprising an application tool, said tool being configured as a pair of tweezers having resilient members each one having a free end and a joined end, said joined ends being mutually connected, said free ends being formed with rounded tips, said resilient members being biased in such manner as to establish a first distance s1 between said free ends when no force is applied to said members, said first distance s1 being larger than said inner tube diameter d1.

12. A kit for tendon repair surgery comprising at least one device as defined in claim 4 and having a nominal inner tube diameter d1, the kit further comprising an application tool, said tool being configured as a pair of tweezers having resilient members each one having a free end and a joined end, said joined ends being mutually connected, said free ends being formed with rounded tips, said resilient members being biased in such manner as to establish a first distance s1 between said free ends when no force is applied to said members, said first distance s1 being larger than said inner tube diameter d1.

13. A kit for tendon repair surgery comprising at least one device as defined in claim 5 and having a nominal inner tube diameter d1, the kit further comprising an application tool, said tool being configured as a pair of tweezers having resilient members each one having a free end and a joined end, said joined ends being mutually connected, said free ends being formed with rounded tips, said resilient members being biased in such manner as to establish a first distance s1 between said free ends when no force is applied to said members, said first distance s1 being larger than said inner tube diameter d1.

14. A kit for tendon repair surgery comprising at least one device as defined in claim 6 and having a nominal inner tube diameter d1, the kit further comprising an application tool, said tool being configured as a pair of tweezers having resilient members each one having a free end and a joined end, said joined ends being mutually connected, said free ends being formed with rounded tips, said resilient members being biased in such manner as to establish a first distance s1 between said free ends when no force is applied to said members, said first distance s1 being larger than said inner tube diameter d1.

15. The method according to claim 8, wherein said tubular sheath has a Young elasticity modulus of 2.8 to 3.2 MPa and an elongation at break of 500 to 600%.

16. The method according to claim 8, wherein said tubular sheath is of substantially frustoconical shape.

17. The method according to claim 8, wherein said tubular sheath further comprises at least one therapeutic agent for stimulating tendon regrowth processes.

18. The method according to claim 17, wherein said therapeutic agent is selected from the group consisting of growth hormones, pharmaceutical agents and growth promoting cells, including stem cells.

19. The method according to claim 17 wherein said fiber mesh comprises hollow fibers containing said therapeutic agent(s).

* * * * *